(12) United States Patent
Ono

(10) Patent No.: US 8,290,010 B2
(45) Date of Patent: Oct. 16, 2012

(54) SURFACE PLASMON GENERATING APPARATUS AND METHOD FOR MAKING THE SAME

(75) Inventor: Tomoki Ono, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 12/784,613

(22) Filed: May 21, 2010

(65) Prior Publication Data

US 2010/0316078 A1    Dec. 16, 2010

(30) Foreign Application Priority Data

Jun. 15, 2009   (JP) ................................ 2009-141774

(51) Int. Cl.
*H01S 5/00* (2006.01)
(52) U.S. Cl. ............... 372/45.01; 372/43.01; 372/46.01; 257/12; 257/46; 257/104
(58) Field of Classification Search ............... 372/45.01; 257/12, 46, 104
See application file for complete search history.

(56) References Cited

U.S. PATENT DOCUMENTS

| | | | |
|---|---|---|---|
| 6,324,199 B1 * | 11/2001 | Capasso et al. | 372/45.01 |
| 2007/0289623 A1 * | 12/2007 | Atwater | 136/252 |
| 2008/0217542 A1 * | 9/2008 | Verma et al. | 250/370.01 |

OTHER PUBLICATIONS

C. F. Bohren, D. R. Huffman; Absorption and Scattering of Light by Small Particles; Wiley Science Paperback Series; pp. 340-341.
K. Okamoto et al.; Surface-plasmon-enhanced light emitters based on InGaN quantum wells; Nature Materials; vol. 3; Sep. 2004.
Mark I Stockman; Spasers explained; Nature Photonics; vol. 2; Jun. 2008.

* cited by examiner

*Primary Examiner* — Yuanda Zhang
(74) *Attorney, Agent, or Firm* — SNR Denton US LLP

(57) ABSTRACT

A surface plasmon-generating apparatus includes an active layer including an n-type region formed on one side and a p-type region formed on the other side, the n-type region and the p-type region being in contact with each other to form a pn junction therebetween; a first barrier layer in contact with a first surface of the active layer; a second barrier layer in contact with a second surface of the active layer, the second surface being opposite the first surface; and a metal body disposed above the pn junction of the active layer with the second barrier layer and an insulating layer therebetween.

4 Claims, 14 Drawing Sheets

NEAR-FIELD LIGHT

ROTATION

SURFACE PLASMON GENERATING APPARATUS AND METHOD FOR MAKING THE SAME

BACKGROUND OF THE INVENTION

1. Field of the Invention

The present invention relates to a surface plasmon-generating apparatus that uses a SPASER (surface plasmon amplification by stimulated emission of radiation) diode and a method for making the surface plasmon-generating apparatus.

2. Description of the Related Art

Surface plasmons (SPs) generated in a metal surface can have a higher wave number than light propagating in air and thus are presently widely used in near-field light applications and nanophotonics, in particular, biosensing. A metal body can have a one-dimensional structure constituted by a flat surface, a two-dimensional structure constituted by stripes and the like, or a three-dimensional structure such as fine particles. In all cases, the wave number of the surface plasmons can be increased by adjusting the length of at least one axis to about several to fifty nanometers. In other words, such metal bodies offer high spatial resolution.

One of processes of generating surface plasmons in such a nano-size three-dimensional metal body (referred to as "nanometal body" hereinafter) is a process of scattering incident light coming from outside.

However, in a non-resonance state, the scattering cross-section area is significantly small and thus the coupling efficiency of incident light to the surface plasmons is low.

It has been reported that when a nanometal body undergoes geometric resonance (cavity) relative to surface plasmons, a high Q value (gain) is obtained. Examples of the structure that undergoes geometric resonance include fine spheres, rods, stripes, and grooves. When the Q value is high, coupling of evanescent light having an intense electromagnetic field generated by surface plasmons to the incident light causes condensation of light, thereby increasing the scattering cross-section area (e.g., refer to C. F. Bohren, D. R. Huffman "Absorption and Scattering of Light by Small Particles" WILEY SCIENCE PAPERBACK SERIES, pp. 340-341). In such a case also, the increase in the scattering cross-section area is about the wavelength of the light. In order to achieve a high coupling efficiency, the incident light is desirably condensed up to the diffraction limit or the positional accuracy is desirably enhanced. However, this involves a complicated system.

Usually, a laser beam is used as the incident light since the resonance frequency width is narrow. Currently, even the semiconductor laser that offers the highest electrical-to-optical power conversion efficiency (EO efficiency) displays only about 40% EO efficiency at the laser output unit in a visible light region. The EO efficiency decreases to several percent after passing through various optical systems. It is thus clear that the electric-to-surface plasmon (E-SP) conversion efficiency will also be significantly low.

It has recently been reported that when a subwavelength local electromagnetic field generated by surface plasmons is near a gain medium having an energy bandgap, energy of electron-hole pairs in the energy bandgap is transferred to the surface plasmons.

For example, when the medium is a semiconductor quantum well, "quantum well-surface plasmon coupling" occurs (refer to K. Okamoto, I. Nimi, A. Shvartser, Y. Narukawa, T. Mukaiand, A. Scherer, "Surface-plasmon-enhanced light emitters based on InGaN quantum wells. "Nature Mat. 3, 601 (2004)). The semiconductor quantum well generates electron-hole pairs by optical excitation and the energy of the electron-hole pairs is transferred to the surface plasmons. Thus, the energy hv of the surface plasmon is either equal to or lower than the energy of the excitation light. In such a state, surface plasmons are incoherent.

When a nanometal body undergoes geometric resonance, stimulated emission of surface plasmons occurs as with light in a resonator, and coherent surface plasmons can be generated. This phenomenon is called SPASER, i.e., surface plasmon amplification by stimulated emission of radiation. For example, a metal shell structure with semiconductor nanodots has been suggested (e.g., refer to M. I. Stockman, "Spasers explained" Nature Photonics 2, 327 (2008)). The gain medium generates electron-hole pairs by optical excitation and the energy of the electron-hole pairs is transferred to the surface plasmons. Thus, the energy hv of the surface plasmons is either equal to or lower than the energy of the excitation light. In any case, as with the case of resonance scattering described above, a highly accurate system for condensing incident light is desirable in order to optically excite the gain medium. Moreover, not all of incident light is absorbed by the gain medium. It is clear that even in the case where a semiconductor laser beam is used as the incident light source, the E-SP efficiency will be significantly low.

Utilization of surface plasmons can be roughly categorized into far-field systems and near-field systems. In the near-field systems in particular, surface plasmons can be used in applications that use high-intensity local light, such as various sensing, capture of fine particles and DNA, information recording devices, and near-field exposure devices. However, there are also disadvantages from the industrial viewpoint, such as that the E-SP efficiency is low, the number of system parts (optical parts in particular) is large, and highly accurate position control of optical systems is desired. Moreover, since not all of the incident light is absorbed in the gain medium, the incident light itself becomes the background noise relative to the local light, resulting in a low S/N ratio.

SUMMARY OF THE INVENTION

It is desirable to increase the E-SP efficiency and decrease the number of system parts (optical parts in particular).

Thus, it is desirable to provide a current-injection-type spaser diode structure that does not need optical parts, increases the E-SP efficiency, and generates nano-scale surface plasmon having high intensity.

According to one embodiment of the present invention, a surface plasmon-generating apparatus includes an active layer including an n-type region formed on one side and a p-type region formed on the other side, the n-type region and the p-type region being in contact with each other to form a pn junction therebetween; a first barrier layer in contact with a first surface of the active layer; a second barrier layer in contact with a second surface of the active layer, the second surface being opposite the first surface; and a metal body disposed above the pn junction of the active layer with the second barrier layer and an insulating layer therebetween.

According to the surface plasmon-generating apparatus above, when an electric current is injected into the pn junction of the active layer, injected electrons and holes efficiently form electron-hole pairs at the pn junction under the metal body and its nearby region. The metal body formed near the active layer in the perpendicular direction receives energy from the electron-hole pairs and generates surface plasmons. Moreover, when the metal body has a structure that can undergo geometric resonance at a wavelength corresponding to the emission spectrum from the pn junction, coherent surface plasmons can be generated. Thus, a current injection-type spaser diode can be formed.

According to another embodiment of the present invention, a method for making a surface plasmon-generating apparatus includes the steps of sequentially layering a first barrier layer of a first conductivity type, an active layer of the first conductivity type, and a second barrier layer of the first conductivity type on a semiconductor substrate of the first conductivity type; forming a region of a second conductivity type opposite to the first conductivity type in a multilayer structure of a first conductivity type including the second barrier layer, the active layer, and the first barrier layer; forming a ridge by patterning the multilayer structure into a ridge shape so that a pn junction between the region of the first conductivity type and the region of the second conductivity type of the multilayer structure is contained in the ridge; forming an insulating film covering the ridge; and forming a metal body extending across the pn junction, the metal body being formed on the insulating film above the pn junction in the ridge.

According to this method, the metal body above the pn junction of the active layer and on the insulating film is formed to extend across the pn junction. Thus, when an electric current is injected into the pn junction of the active layer, injected electrons and holes efficiently form electron-hole pairs at the pn junction under the metal body and its nearby region. The metal body formed near the active layer in the perpendicular direction receives energy from the electron-hole pairs and generates surface plasmons.

Since the surface plasmon-generating apparatus above can directly generate surface plasmons by current injection, the electric-to-surface plasmon conversion (E-SP) efficiency can be increased.

Since the method for making the surface plasmon-generating apparatus above can directly generate surface plasmons by current injection, the electric-surface plasmon conversion (E-SP) efficiency can be increased.

DESCRIPTION OF THE PREFERRED EMBODIMENTS

Embodiments of the present invention will now be described.

1. First Embodiment

Example Structures of Surface Plasmon-Generating Apparatus

Figure 1:
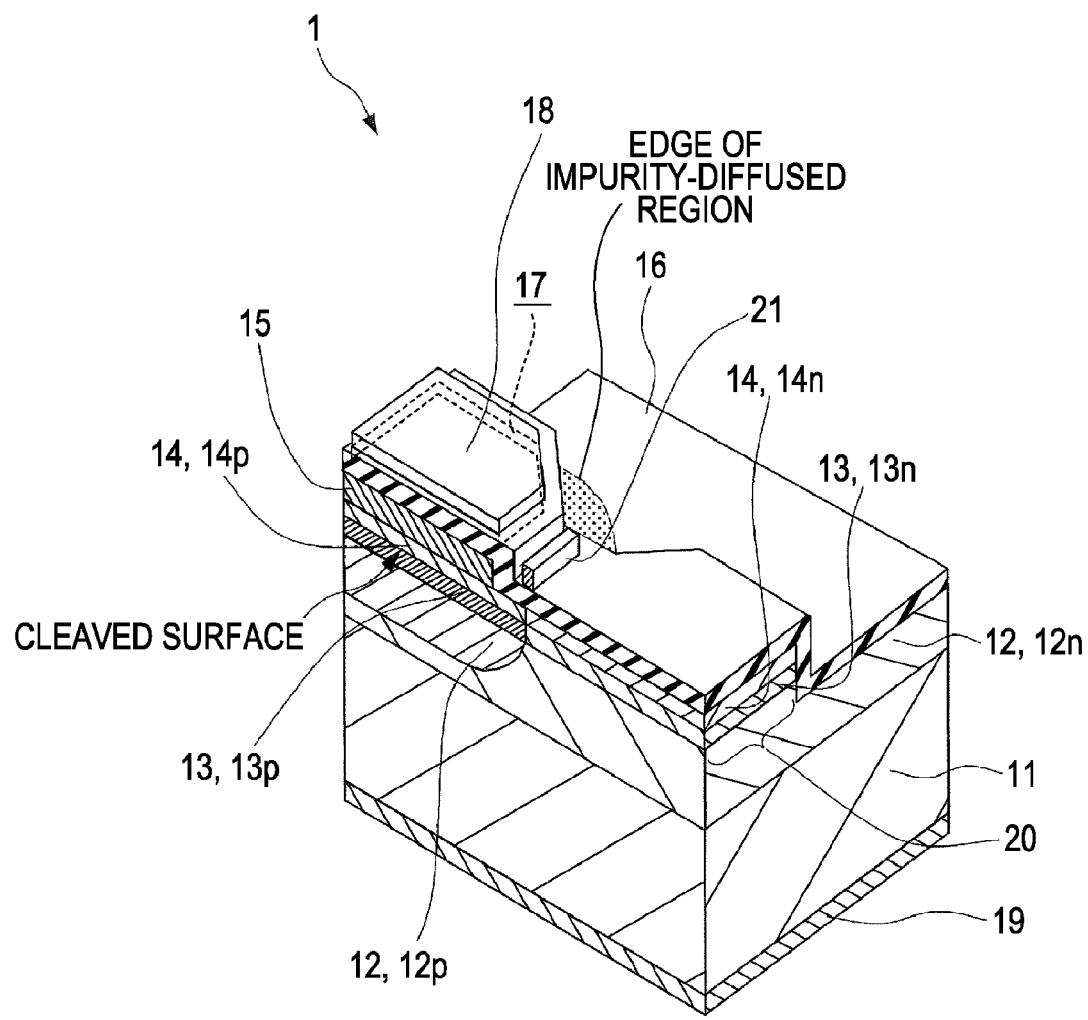
FIG. 1 is a schematic perspective cross-sectional view of an example of a structure of a surface plasmon-generating apparatus according to a first embodiment.

An example of a structure of a surface plasmon-generating apparatus according to a first embodiment is described with reference to a schematic perspective cross-sectional view of FIG. 1 and a partial enlarged perspective cross-sectional view of FIG. 2. In FIG. 1, the basic structure of a surface plasmon-generating apparatus is shown.

Figure 2:
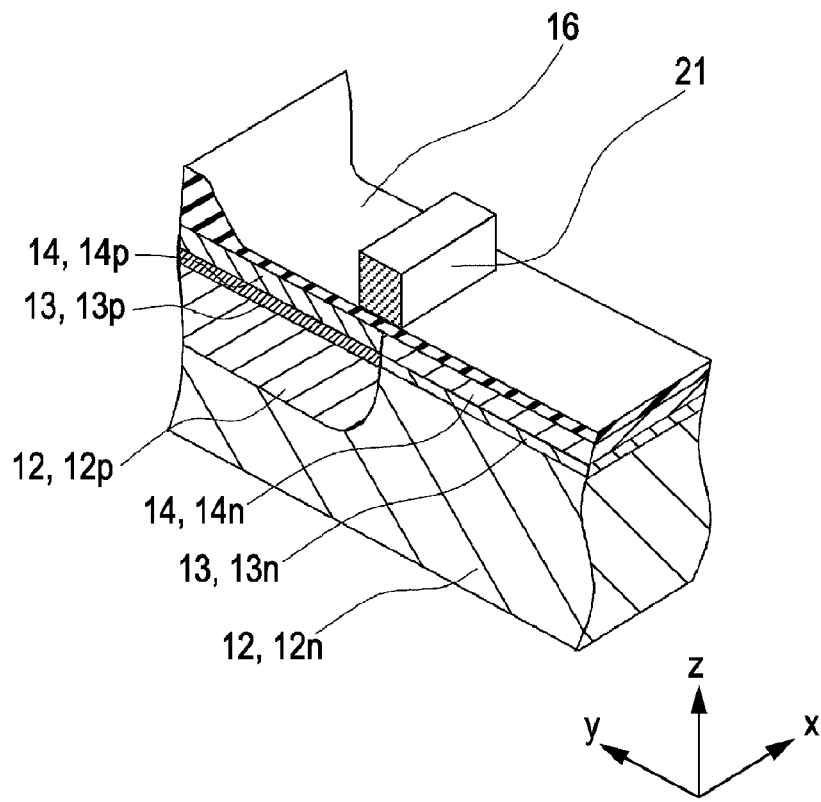
FIG. 2 is an enlarged perspective cross-sectional view of a part of FIG. 1.

Referring to FIGS. 1 and 2, the surface plasmon-generating apparatus includes a substrate 11. The substrate 11 is, for example, an n-type gallium arsenide (n-GaAs) substrate. A first barrier layer 12, an active layer 13, and a second barrier layer 14 are sequentially layered on one of the surfaces of the substrate 11.

The first barrier layer 12 is formed at a first surface side of the active layer 13 and is composed of a semiconductor having a bandgap energy larger than the bandgap energy of the active layer 13. An example of such a semiconductor is aluminum gallium indium phosphide (AlGaInP).

The active layer 13 is a gallium indium phosphide (GaInP) layer having a pn junction. In other words, a p-type active layer 13p is formed on one side and an n-type active layer 13n is formed on the other side to form a pn junction. This pn junction is a homojunction.

The second barrier layer 14 is formed at a second surface side (opposite the first surface side) of the active layer 13 and is composed of a semiconductor having a bandgap energy larger than the bandgap energy of the active layer 13. An example of such a semiconductor is aluminum gallium indium phosphide (AlGaInP).

The second barrier layer 14, the active layer 13, and an upper portion of the first barrier layer 12 form a ridge 20. The width of the portion including the pn junction and its nearby regions is decreased to form a restricting structure.

A part of the first barrier layer 12 and a part of the second barrier layer 14 that sandwich the p-type active layer 13p are p-type regions. In other words, the p-type active layer 13p (e.g., p-GaInP layer) is sandwiched between a p-type first barrier layer 12p (e.g., p-AlGaInP layer) and a p-type second barrier layer 14p (e.g., p-AlGaInP layer).

Similarly, a part of the first barrier layer 12 and a part of the second barrier layer 14 that sandwich the n-type active layer 13n are n-type regions. In other words, the n-type active layer 13n (e.g., n-GaInP layer) is sandwiched between an n-type first barrier layer 12n (e.g., n-AlGaInP layer) and an n-type second barrier layer 14n (e.g., n-AlGaInP layer).

The p-type regions are formed by diffusing a p-type impurity, zinc, into the n-type regions described above. Naturally, any p-type impurity other than zinc may be used. For example, magnesium may be used.

Alternatively, the first barrier layer 12, the active layer 13, and the second barrier layer 14 can have the following features.

For example, an aluminum gallium arsenide (AlGaAs) layer may be used as the first barrier layer 12, a gallium arsenide (GaAs) layer may be used as the active layer 13, and a gallium indium phosphide (GaInP) layer may be used as the second barrier layer 14.

This active layer 13 composed of GaAs has a pn junction. In other words, a p-GaAs layer is formed as the p-type active layer 13p on one side and an n-GaAs layer is formed as the n-type active layer 13n on the other side to form a pn junction. This pn junction is a homojunction.

A part of the first barrier layer 12 and a part of the second barrier layer 14 that sandwich the p-type active layer 13p are p-type regions. In other words, the p-type active layer 13p (p-GaAs layer) is sandwiched between the p-type first barrier layer 12p (p-AlGaAs layer) and the p-type second barrier layer 14p (p-GaInP layer).

Similarly, a part of the first barrier layer 12 and a part of the second barrier layer 14 that sandwich the n-type active layer 13n are n-type regions. In other words, the n-type active layer 13n (n-GaAs layer) is sandwiched between the n-type first barrier layer 12n (n-AlGaAs layer) and the n-type second barrier layer 14n (n-GaInP layer).

The p-regions (p-type first barrier layer 12p, p-type active layer 13p, and p-type second barrier layer 14p) are formed by diffusing a p-type impurity, zinc, into the n-type regions described above, for example.

The p-type first barrier layer 12p also lies in the first barrier layer 12 on a lateral side of the ridge 20 (lateral side of the n-type first barrier layer 12n). The n-type first barrier layer 12n also lies in the depth direction of the p-type first barrier layer 12p. In other words, the p-type first barrier layer 12p is formed in part of the upper part of the n-type first barrier layer 12n.

Accordingly, the pn junction between the p-type active layer 13p and the n-type active layer 13n, the pn junction between the p-type first barrier layer 12p and the n-type active layer 13n, and the pn junction between the p-type second barrier layer 14p and the n-type second barrier layer 14n are located in the same position in a plan view.

A p-type cap layer 15 is formed on the p-type second barrier layer 14p.

An insulating film 16 is formed on the first barrier layer 12 and the multilayer structure including the p-type cap layer 15, the second barrier layer 14, the active layer 13, and the first barrier layer 12. The insulating film 16 is, for example, a silicon oxide film. The insulating film 16 may be any insulating film that has an imaginary part of complex index of refraction of 0.1 or less. For example, titanium oxide ($TiO_2$), aluminum oxide ($Al_2O_3$), zinc oxide (ZnO), hafnium oxide ($HfO_2$), silicon nitride (SiN), aluminum nitride (AlN), magnesium oxide (MgO), and tantalum oxide ($Ta_2O_5$) may be used.

An opening 17 is formed in the insulating film 16 on the p-type cap layer 15. A p electrode 18 that connects to the p-type cap layer 15, which serves as a p-type contact layer, through the opening 17 is formed on the insulating film 16. In other words, the p-type cap layer 15 serves as a p-type contact layer between the second barrier layer 14 and the p electrode 18. The p electrode 18 has a multilayer structure including, in order from the bottom, a titanium film, a platinum film, and a metal film, for example.

An n electrode 19 is formed on the other surface of the substrate 11. In other words, the substrate 11 serves as an n-type contact layer between the first barrier layer 12 and the n electrode 19. The n electrode 19 has a multilayer structure including, in order from the substrate 11 side, a gold germanium film, a nickel film, a gold film, a titanium film, a platinum film, and a gold film. This structure is merely an example and any other structure may be employed.

A metal body 21 is formed on the insulating film 16 above the pn junction in the active layer 13. The metal body 21 is a three-dimensional metal body having nanometer order sizes. Hereinafter, this metal body 21 is referred to as a nanometal body 21.

The distance between the nanometal body 21 and the active layer 13 is preferably the wavelength or less and more preferably 20 nm or less. Thus, the thickness of the insulating film 16 is preferably the wavelength or less and more preferably 20 nm or less. The nanometal body 21 is located at a position isolated from the p-type cap layer 15, the p electrode 18, and the n electrode 19.

The nanometal body 21 may be composed of a single metal such as gold (Au), silver (Ag), aluminum (Al), or the like or an alloy that contains as a main component at least one metal selected from gold (Au), silver (Ag), and aluminum (Al). The nanometal body 21 may contain at least one metal selected from platinum (Pt), nickel (Ni), and palladium (Pd).

Although not shown in the drawing, a surface plasmon-generating apparatus 1 may include a buffer layer between the substrate 11 and the first barrier layer 12, the buffer layer including a gallium arsenide (GaAs) layer, an aluminum gallium arsenide (AlGaAs) layer, and a gallium indium phosphide (GaInP) layer, for example. An aluminum gallium indium phosphide (AlGaInP) layer or an aluminum indium phosphide (AlInP) layer having a bandgap larger than that of the first barrier layer 12 may also be formed.

The edge of the impurity-diffused region of the p-type first barrier layer 12p may lie within the first barrier layer 12 on the lateral side of the ridge 20.

An intermediate layer (not shown) composed of gallium indium phosphide (GaInP) or aluminum gallium arsenide (AlGaAs) may be formed between the p-type second barrier layer 14p and the p-type cap layer 15.

An electron barrier layer (not shown) formed of a p-type aluminum indium phosphide (p-AlInP) layer or a p-type aluminum gallium indium phosphide (p-AlGaInP) may be formed between the p-type second barrier layer 14p and the p-type cap layer 15. When the second barrier layer 14 is composed of AlGaInP, a p-AlInP layer is used as the electron barrier layer. When the second barrier layer 14 is composed of GaInP, a p-AlGaInP layer is used as the electron barrier layer.

The resonant frequency of the nanometal body 21 ranges from the visible light range to infrared range according to the size and the structure of the nanometal body 21. That is, surface plasmons with various wavelengths can be generated by selecting the material of the active layer 13 so that the resonant frequency of the nanometal body 21 is within the spontaneous emission spectrum of the active layer 13 not provided with the nanometal body 21.

Examples of such semiconductor material systems include, in addition to GaInP and GaAs, group 13-15 (III-V) systems such as GaN, InGaN, AlGaN, GaP, GaAsP, AlGaAs, GaInAs, GaInPAs, InP, InAs, and AlAs, and group 2-12-16 and 12-16 (II-VI) systems such as ZnSe, ZnSSe, BeMgZnSe, BeZnSe, ZnCdSe, ZnO, and ZnMgO.

Next, the shape, the arrangement, etc., of the nanometal body 21 are described in detail.

Figure 3:
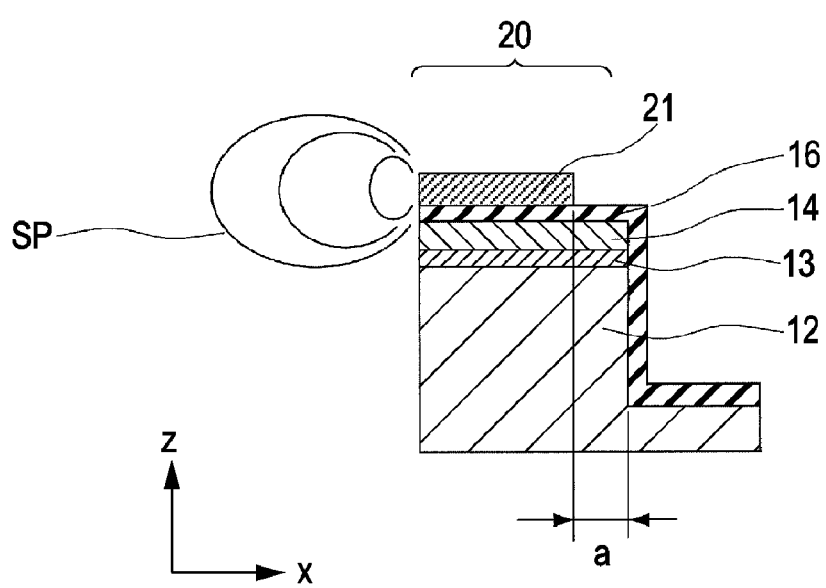
FIG. 3 is a cross-sectional view of a metal body shown in FIG. 1 taken at an x-z plane passing through the metal body.

Referring to a cross-sectional view of FIG. 3 taken at the x-z plane passing through the nanometal body 21 shown in FIG. 1, the width of the ridge 20 is preferably about the same as the width of the nanometal body 21. For example, the distance a between one end of the nanometal body 21 and an upper side surface end of the ridge 20 is preferably 10 μm or less. When the distance a is 10 μm or less, electrons and holes in the homojunction at the lower outer side of the nanometal body 21 have short lifetime by surface plasmon excitation and are thus transversally diffused into the homojunction under the nanometal body 21. Thus, dead emission that does not contribute to surface plasmon excitation rarely occurs.

The wave number of the surface plasmons SP generated in the nanometal body 21 at the plane in contact with the insulating film 16 depends on the size of the nanometal body 21. Thus, the size of the nanometal body 21 is not singularly determined and is preferably selected according to the usage.

For example, in order to obtain a high resolution, the metal film thickness of the nanometal body 21 is preferably 3 nm or more and 20 nm or less.

Since the surface plasmons SP having a wave number several times that of light in air has a propagation length of about 1 μl, when the length of the nanometal body 21 in the longitudinal direction of the ridge 20 is sufficiently larger than 1 μm, surface plasmons that do not contribute to the local electromagnetic field generated at the end face of the nanometal body 21 exist inside the nanometal body 21.

When the nanometal body 21 is a metal film having a thickness of, for example, about 100 nm, the metal film serves as a bulk having a semi-infinite thickness relative to surface plasmons SP generated in the plane in contact with the insulating film 16 and the propagation length will exceed 10 μm.

When the nanometal body 21 is shorter than the propagation length of the surface plasmons SP, the surface plasmons SP may be amplified by resonance. The form of the nanometal body 21 is not limited to a rectangular parallelepiped shown in FIGS. 1 to 3 and may be a fine sphere, an ellipsoid, an assembly, or the like. When the nanometal body 21 induces geometric resonance of the surface plasmons SP, the Q value of the surface plasmons SP rises and the E-SP efficiency increases.

The structures of the nanometal body 21 that achieves such a high Q value are described below.

MODIFICATIONS

Example Structures of Nanometal Body

Specific example structures of the nanometal body will now be described.

Modification Example 1

Nanometal Body Constituted by a Single Dot Plate

As shown in FIGS. 4A to 4K, the nanometal body 21 may be a single dot plate having a circular, elliptic, or polygonal shape when view from above, for example.

Figure 4A:
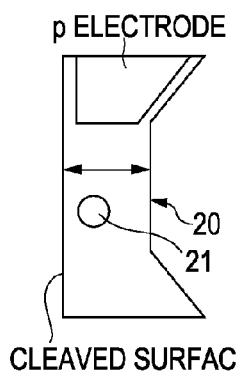
FIGS. 4A to 4k are plan views illustrating modification examples of nanometal bodies.

The nanometal body 21 shown in FIG. 4A is a single dot plate having a circular shape in a plan view.

Figure 4B:
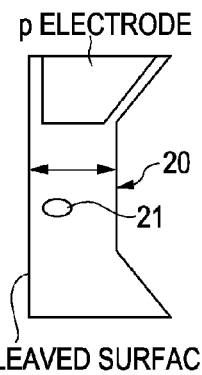
Figure 4C:
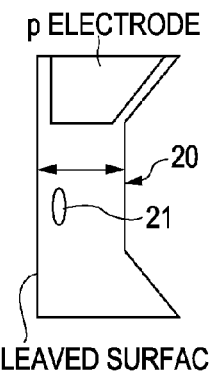
Figure 4D:
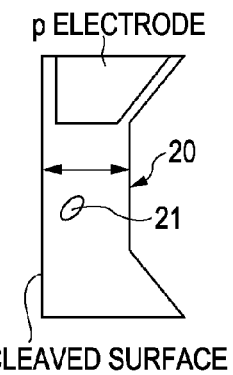

The nanometal bodies 21 shown in FIGS. 4B to 4D are each a single dot plate having an elliptic shape in a plan view. The major axis direction of the ellipse may be parallel, right-angled, or at any angle (e.g., 45°) with respect to the width direction (the direction indicated by the double-headed arrow) of the ridge 20.

Figure 4E:
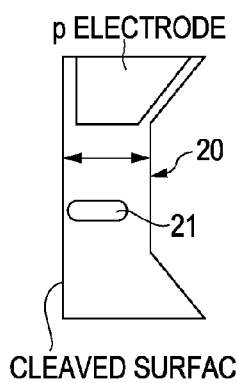
Figure 4F:
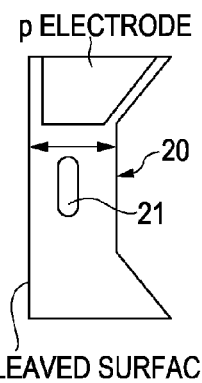

The nanometal bodies 21 shown in FIGS. 4E and 4F are each a single dot plate having an oval shape in a plan view. The major axis direction of the oval may be parallel, right-angled, or at any angle (e.g., 45°) with respect to the width direction (the direction indicated by the double-headed arrow) of the ridge 20.

Figure 4G:
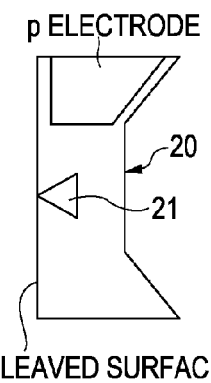

The nanometal body 21 shown in FIG. 4G is a single dot plate having a triangular shape in a plan view. In the sate shown in the drawing, one apex is facing the end surface side of the ridge 20 but the direction of the triangle is not limited to this.

Figure 4H:
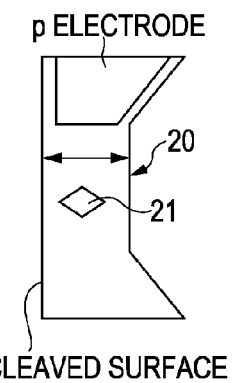

The nanometal body 21 shown in FIG. 4H is a single dot plate having a parallelogram shape in a plan view. The direction of the longer diagonal of the parallelogram may be parallel, right-angled, or at any angle (e.g., 45°) with respect to the width direction (the direction indicated by the double-headed arrow) of the ridge 20.

Figure 4I:
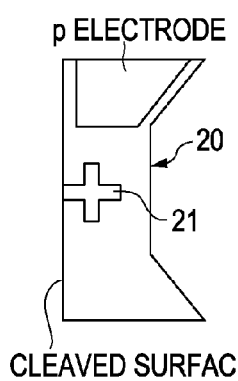
Figure 4J:
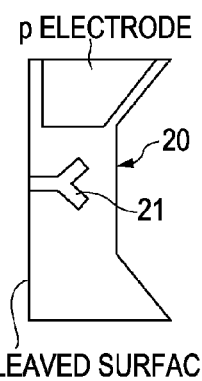
Figure 4K:
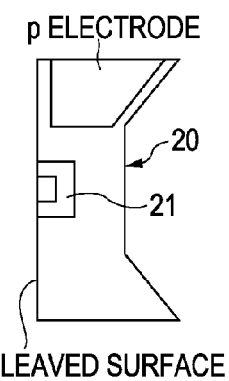

The nanometal body 21 may be a single dot plate having a cross shape in a plan view as shown in FIG. 4I, a single dot plate having a letter-Y shape in a plan view as shown in FIG. 4J, or a single dot plate having a square bracket shape in a plan view as shown in FIG. 4K.

The thickness of the nanometal body 21 may be, for example, several nanometers, e.g., 3 nm so that the nanometal body 21 is formed as a thin film, or several micrometers, e.g., 5 μm so that the nanometal body 21 is formed as a thick film. When the nanometal body 21 is a thin film, the surface plasmons generated above and under the nanometal body 21 are coupled whereas when the nanometal body 21 is a thick film, surface plasmons generated in the lower surface of the nanometal body 21 travel around so that the surface plasmons are also generated in the upper surface of the nanometal body 21.

The short part of each of the nanometal bodies 21 shown in FIGS. 4A to 4K (when the nanometal body 21 is circular, this is the diameter; when the nanometal body 21 is elliptical, this is the minor axis; and when the nanometal body 21 is polygonal, this is the short side of the smallest rectangle that can contain the polygon) is equal to or smaller than the wavelength.

When the nanometal body 21 is elliptical as shown in FIGS. 4B to 4D, the frequency and the field vector of the near-field light generated near the cleaved surface change according to the angle defined by the cleaved surface and the major axis. When a tip of the nanometal body 21 is located near the cleaved surface as in the nanometal bodies 21 shown in FIGS. 4G and 4H, the intensity of the near-field light is increased by concentration of the surface plasmons.

The structures shown in FIGS. 4A to 4K can also be used in applications that utilize near-field light from wafer surfaces. Since the surface plasmons generated in these nanometal bodies 21 are rarely converted to propagating light, the surface plasmon-generating apparatus 1 (spaser diode) of this embodiment is suitable for use in a near region.

Modification Example 2

Examples of Three-Dimensional Shapes of Nanometal Body

Examples of three-dimensional shapes of the nanometal body 21 will now be described with reference to FIGS. 5A to 5D. As shown in FIGS. 5A to 5D, the nanometal body 21 is a single fine object spherical, cylindrical, or conical in shape, for example.

Figure 5A:
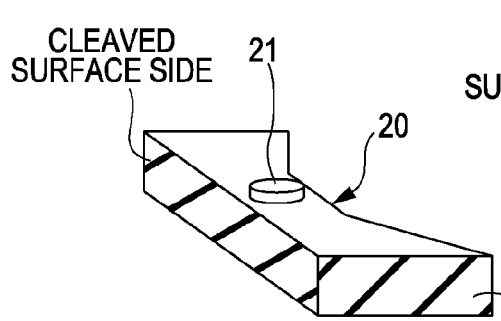
FIGS. 5A to 5D are perspective views illustrating modification examples of nanometal bodies.

As shown in FIG. 5A, the nanometal body 21 may be a short cylinder formed on the surface of the insulating film 16 of the ridge 20.

Figure 5B:
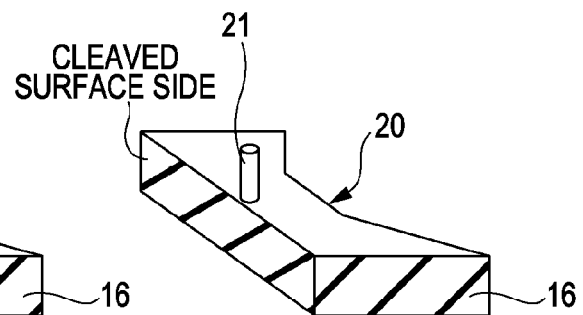

As shown in FIG. 5B, the nanometal body 21 may be a long cylinder vertically placed on the surface of the insulating film 16 of the ridge 20.

Figure 5C:
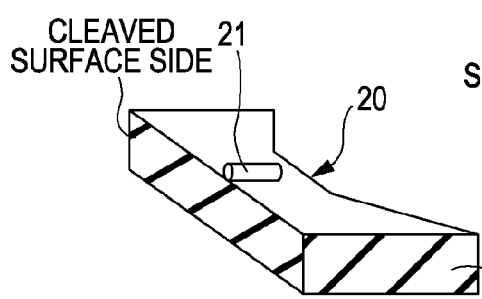

As shown in FIG. 5C, the nanometal body 21 may be a long cylinder laid on its side on the surface of the insulating film 16 of the ridge 20.

Figure 5D:
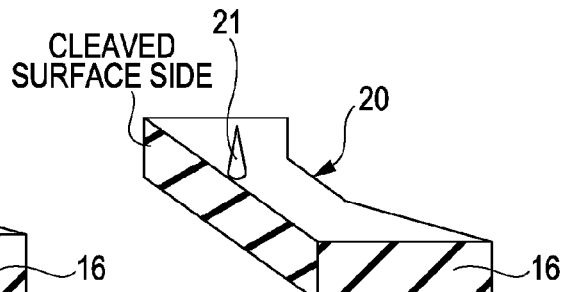

As shown in FIG. 5D, the nanometal body 21 may be a cone formed on the surface of the insulating film 16 of the ridge 20.

The height of each of the nanometal bodies 21 is several nanometers to several hundred nanometers, e.g., about 3 nm or more and about 300 nm or less. The length of the short part of each nanometal body 21 is equal to or lower than the wavelength.

As shown in FIGS. 5B and 5C, when the arrangement of the cylinder is changed, the frequency and the field vector of the near-field light generated near the cleaved surface are also changed.

The structures shown in FIGS. 5C and 5D are particularly suited to usages that utilize near-field light from wafer surfaces. Since the surface plasmons generated in these nanometal bodies 21 are rarely converted to propagating light, the surface plasmon-generating apparatus 1 (spaser diode) is suitable for use in a near region.

Modification Example 3

Examples of Metal Body Constituted by Combination of Fine Parts

The nanometal body 21 may be constituted by a combination of a small number of dot plates or fine bodies. Examples thereof will now be described with reference to FIGS. 6A to 6J.

Figure 6A:
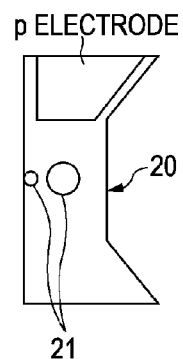
FIGS. 6A to 6J are plan views illustrating modification examples of nanometal bodies.
Figure 6B:
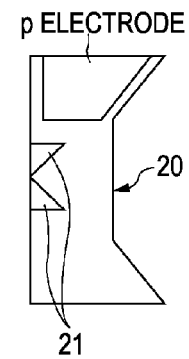
Figure 6C:
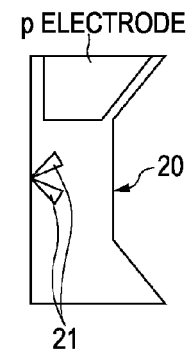
Figure 6D:
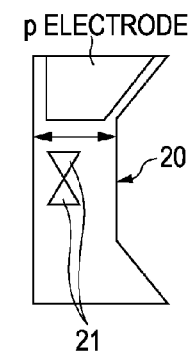
Figure 6E:
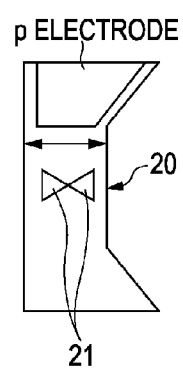

As shown in FIG. 6A, the nanometal body 21 may be constituted by circular plates of different sizes arranged to be close to each other. According to this structure, the frequency at which the intensity of the surface plasmons is increased may exist in the smaller circular plate and thus a strong near-field can be generated.

Examples of other structures that can achieve the same effect include bowtie-like structures shown in FIGS. 6B to 6E, in which two triangles are arranged so that the apexes are near each other. Although not shown in the drawings, three or more triangles may be arranged so that the apexes are near one another.

Figure 6F:
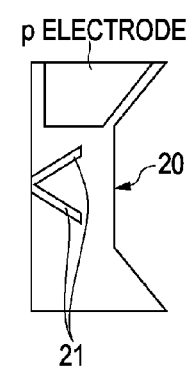
Figure 6G:
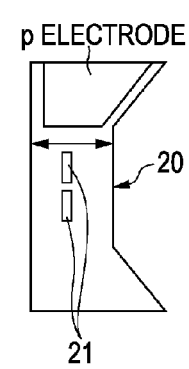
Figure 6H:
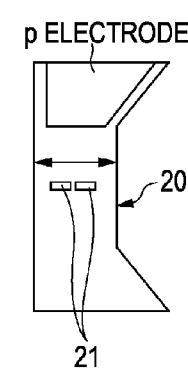
Figure 6I:
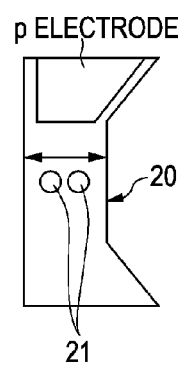
Figure 6J:
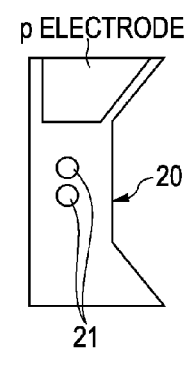

As shown in FIG. 6F, two elongated parallelograms may be arranged so that ends thereof are close to each other. As shown in FIGS. 6G and 6H, two elongated rectangles may be arranged so that short sides thereof are close to each other. As shown in FIGS. 6I and 6J, two circular plates may be arranged to be close to each other.

According to the structures shown in FIGS. 6D, 6E, and 6G to 6J, the direction in which the nanometal bodies 21 are arranged may be parallel, right-angled, or at any angle with respect to the width direction (the direction indicated by the double-headed arrow) of the ridge 20.

Modification Example 4

Examples of Nanometal Body Constituted by Single Dot Plate with Hole Therein

In applications that use near-field light at the wafer surface, the nanometal body 21 may be a metal thin film 21p with one or more openings 21h as shown in FIGS. 7A to 7G.

Figure 7A:
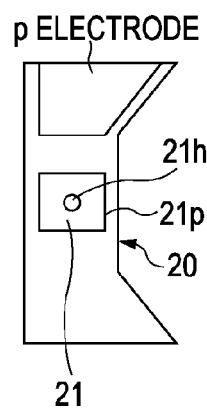
FIGS. 7A to 7G are plan views illustrating modification examples of nanometal bodies.
Figure 7B:
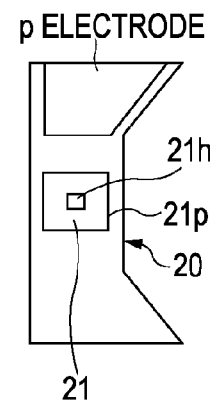
Figure 7C:
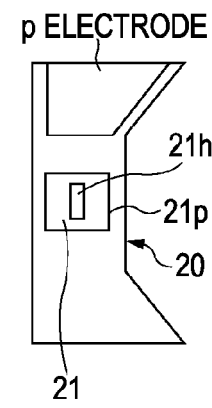

For example, the opening 21h shown in FIG. 7A has a circular shape in a plan view. The opening 21h shown in FIG. 7B has a square shape in a plan view. The opening 21h shown in FIG. 7C has a rectangular shape in a plan view.

Figure 7D:
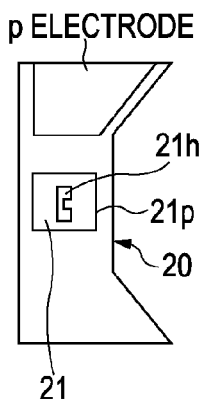

The opening 21h shown in FIG. 7D is formed as a single ridge opening that has a rectangular shape in a plan view with a rectangular projection extending inward from a long side of the rectangle.

Figure 7E:
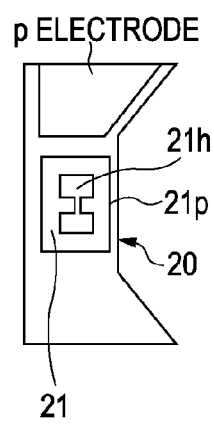

The opening 21h shown in FIG. 7E is formed as a double ridge opening that has a rectangular shape in a plan view with two rectangular projections respectively extending inward from two long sides of the rectangle.

Figure 7F:
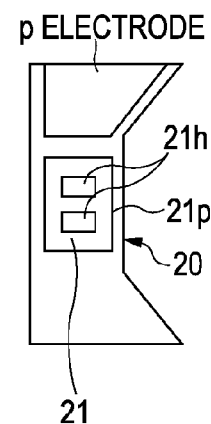

For example, the openings 21h shown in FIG. 7F each have a rectangular shape in a plan view and are spaced from each other. The direction in which the rectangular openings are arranged may be parallel, right-angled, or at any angle with respect to the width direction (the direction indicated by the double-headed arrow) of the ridge 20.

Figure 7G:
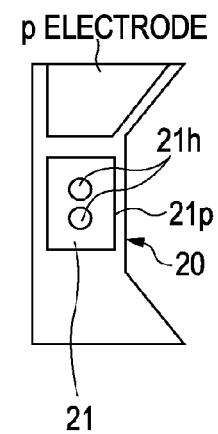

The openings 21h shown in FIG. 7G each have a circular shape in a plan view and are spaced from each other. The direction in which the circular openings are arranged may be parallel, right-angled, or at any angle with respect to the width direction (the direction indicated by the double-headed arrow) of the ridge 20.

According to the structures shown in FIGS. 7D to 7G, intense near-field light can be generated at the ridge 20 or between two openings.

Modification Example 5

Examples of Metal-Core Waveguide Constituting Nanometal Body

The nanometal body 21 may be formed by a metal-core waveguide. As shown in FIGS. 8A to 8D, the cross-sectional shape of the metal core may be circular, elliptical, or polygonal, for example.

Figure 8A:
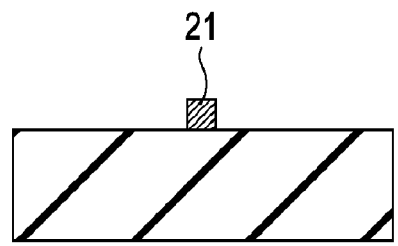
FIGS. 8A to 8D are cross-sectional views illustrating modification examples of nanometal bodies.
Figure 8B:
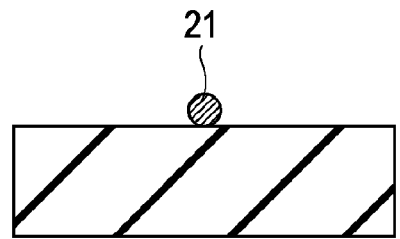
Figure 8C:
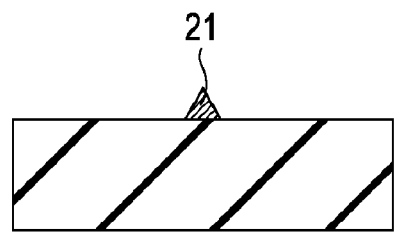

The cross-sectional shape of the metal core constituting the nanometal body 21 shown in FIG. 8A is rectangular. The cross-sectional shape of the metal core constituting the nanometal body 21 shown in FIG. 8B is circular. The cross-sectional shape of the metal core constituting the nanometal body 21 shown in FIG. 8C is triangular.

Figure 8D:
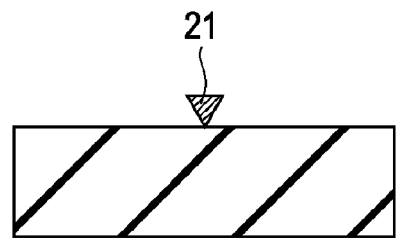

The cross-sectional shape of the metal core constituting the nanometal body 21 shown in FIG. 8D is inverted triangular.

When the short part of the cross-section of the metal core constituting the nanometal body 21 is sufficiently smaller than the wavelength, the wave number of the surface plasmons increases significantly. However, in general, such a metal waveguide has two or more surface plasmon modes. A waveguide having a finite length as described above tends to achieve a high Q by a mode of a smaller wave number. This is because the propagation length of the mode is large. Each mode has its own resonant frequency.

In a range where the resonant frequency overlaps the spontaneously emitted light from the active layer (refer to FIGS. 1 and 2), the efficiency of converting the electron-hole pairs to surface plasmons is high.

Thus, the mode that considers both the Q value and the conversion efficiency tends to be excited.

Since the resonant frequency can be adjusted by the metal core material, the surrounding dielectric material, and the complex dielectric constant of the semiconductor, the resonant frequency is designed to suit the intended application.

Modification Example 6

Examples of Two-Dimensional Shapes of Metal Core Constituting Nanometal Body

The state of the nanometal bodies 21 constituted by the metal cores described above when viewed from above will now be described with reference to plan views in FIGS. 9A to 9G.

Figure 9A:
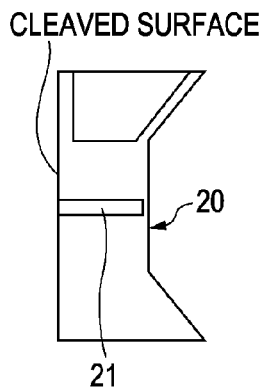
FIGS. 9A to 9G are plan views illustrating modification examples of nanometal bodies.

For example, the nanometal body 21 shown in FIG. 9A has a straight line shape. The nanometal bodies 21 shown in FIGS. 9B and 9C each have a bent shape. The nanometal body 21 shown in FIG. 9D has a cross shape. The nanometal body 21 shown in FIG. 9E has a ring shape. The nanometal body 21 shown in FIG. 9F has a parallelogram shape. The nanometal body 21 shown in FIG. 9G has an angular U shape.

Figure 9B:
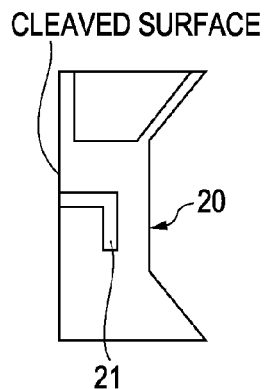
Figure 9C:
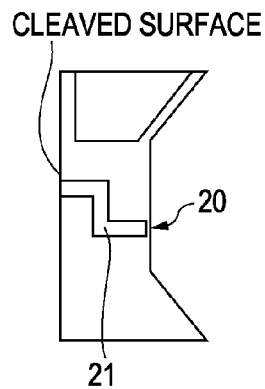

Reflection of propagating surface plasmons occurs at the bent portion of the nanometal bodies 21 shown in FIGS. 9B and 9C. Thus, the Q value of the dot row positioned above the active layer improves and the efficiency of a spaser diode increases.

FIG. 9C shows the state in which the metal core constituting the nanometal body 21 is bent twice but the number of times the metal core is bent may be more than two. The angle of bending is not limited to 90° and may be more than or less than 90°. However, as the bent angle becomes obtuse, the effect brought about by bending decreases. Moreover, when the bent angle is acute, more intense near-field light can be generated. In particular, when the bent portion is located near the cleaved surface, more intense near-field light can be generated.

Figure 9D:
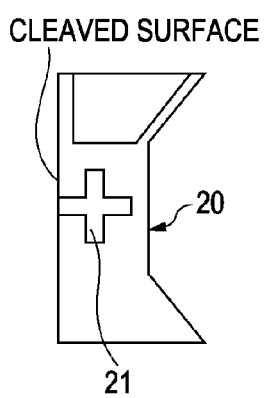

As shown in FIG. 9D, waveguides may intersect each other, for example, the nanometal body 21 may have a cross shape. When the nanometal body 21 has a cross shape in a plan view and the near-field light from the cleaved surface is to be utilized, the resonance spectrum can be shaped.

Figure 9E:
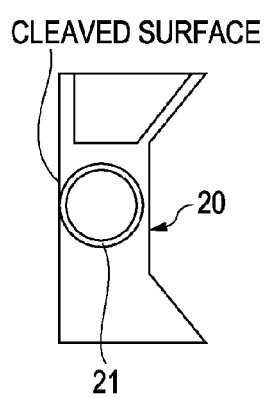
Figure 9F:
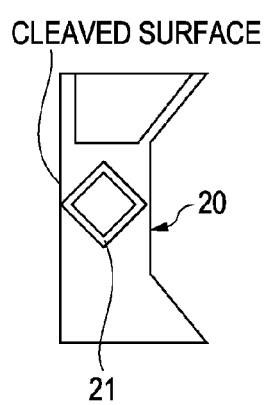
Figure 9G:
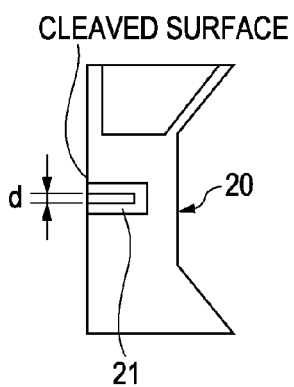

As shown in FIGS. 9E and 9F, the metal-core waveguide constituting the nanometal body 21 may have a closed structure, e.g., a ring shape. Since a ring-shaped resonator is formed by this structure, the Q value is increased.

As shown in FIG. 9F, when a closed resonator has edges, intense near-field light is sometimes generated. In particular, an edge of the nanometal body 21 is preferably positioned near the cleaved surface of the ridge 20.

As shown in FIG. 9F, the front end and the back end of the metal-core waveguide constituting the nanometal body 21 may be positioned in the cleaved surface of the ridge 20. When the spacing d between the front and back ends is equal to or less than the wavelength, intense near-field light is generated between parts of the waveguide due to mode coupling.

Modification Example 7

Examples of Nanometal Body Constituted by Metal-Film Waveguide Using Nonmetal Core The structure in which the nanometal body 21 is constituted by a metal-film waveguide will now be described with reference to FIGS. 10A to 10E.

For example, as shown in FIGS. 10A to 10E, a nonmetal core 21c is a slit formed in the metal film. The cross-sectional shape of the nonmetal core 21c may be circular, elliptical, semicircular, triangular, rectangular, or polygonal, for example.

Figure 10A:
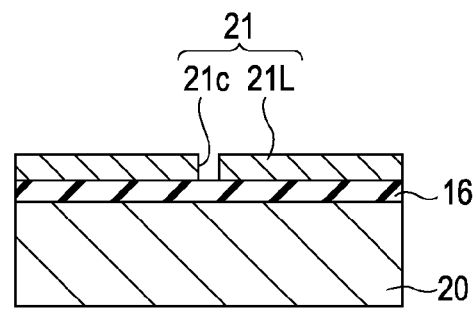
FIGS. 10A to 10E are cross-sectional views illustrating modification examples of nanometal bodies.
Figure 10B:
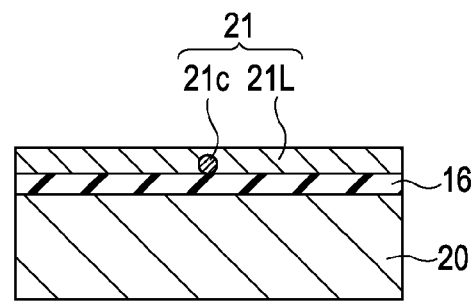
Figure 10C:
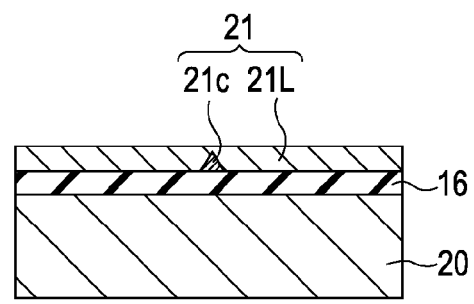
Figure 10D:
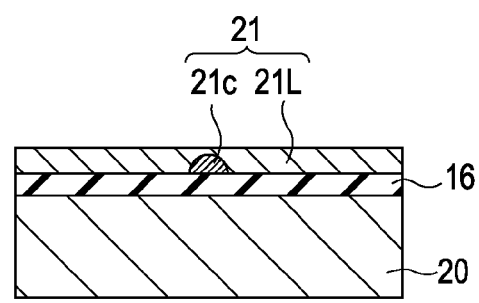
Figure 10E:
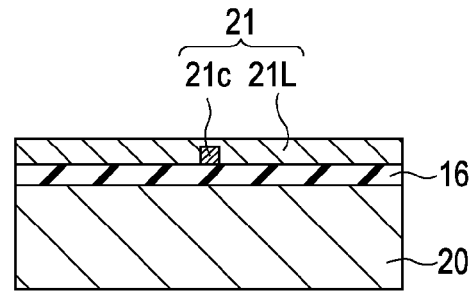

For example, as shown in FIG. 10A, metal films 21L having uniform thickness are formed with a particular space therebetween on the insulating film 16 on the ridge 20. The space is formed as a slit and functions as a nonmetal core 21c. In other word, the nonmetal core 21c is a space in this example.

The most basic surface plasmons are generated at the interface between a uniform metal film and a dielectric body. Thus, even with the structure shown in FIG. 10A, a waveguide mode is established.

A waveguide mode can be formed in a slit not only when the cross-sections of the metal films 21L are closed relative to the nonmetal core 21c but also when the side end faces of the metal films 21L are close to each other and form a slit.

Fabrication of a metal film structure in which the cross-section of the slit is not closed by the metal films 21L is easy. For example, a metal film 21L may be formed on the insulating film 16 and then etched to form a nonmetal core 21c constituted by a slit having a width of several nanometers to less than a micrometer.

As shown in FIGS. 10B to 10E, the nanometal body 21 may be formed by covering a nonmetal core 21c on the insulating film 16 with a metal film 21L, the metal core 21 being composed of a dielectric material and having a circular, triangular, semicircular, or rectangular cross-section or the like.

The structures shown in FIGS. 10B to 10E can be formed simply by forming the metal film 21L over the nonmetal core 21c formed on the insulating film 16.

Such waveguides generally have the same functions and properties as the metal-core waveguides described with reference to FIGS. 8A to 8D and are thus designed to suit the application as described above. The shape of the waveguide from above (in a plan view) is similar to the shapes shown in plan views of FIGS. 9A to 9G.

Modification Example 8

Examples of Nanometal Body Constituted by Metal-Film Waveguide

Next, structures of waveguides in which a recess formed in the insulating film 16 is filled with the metal film 21L to form the nanometal body 21 are described with reference to FIGS. 11A and 11B.

Figure 11A:
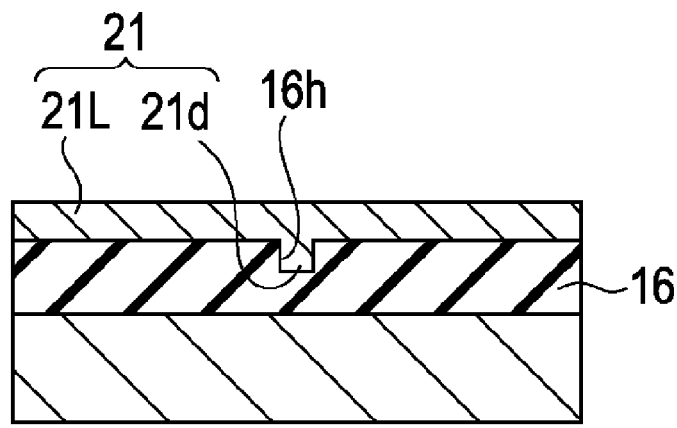
FIGS. 11A and 11B are cross-sectional views illustrating modification examples of nanometal bodies.
Figure 11B:
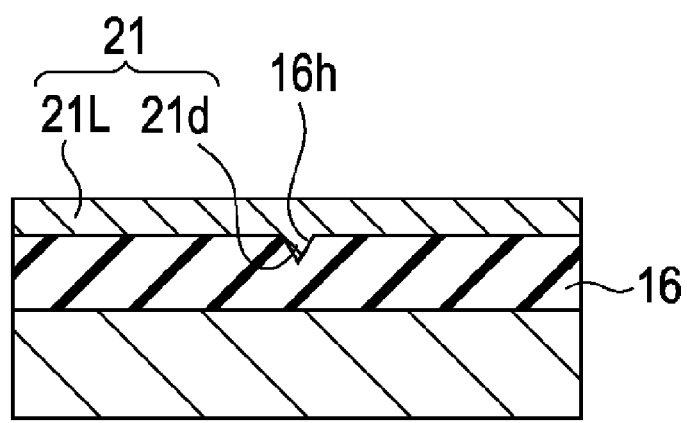

For example, as shown in FIGS. 11A and 11B, a recess 16h having a rectangular or inverted triangular cross-sectional shape is formed on the surface side of the insulating film 16. A metal film 21L is formed on the insulating film 16 so as to bury the recess 16h. In other words, a protrusion 21d having a rectangular or inverted triangular cross-sectional shape and being formed on the lower surface of the metal film 21L protrudes into the upper part of the insulating film 16.

This structure can be fabricated by forming a metal film 21L over the recess 16h formed in the insulating film 16.

Such waveguides generally have the same functions and properties as the metal-core waveguides described with reference to FIGS. 8A to 8D and are thus designed to suit the application as described above. The shape of the waveguide from above (in a plan view) is similar to the shapes shown in plan views of FIGS. 9A to 9G.

Modification Example 9

Examples of Nanometal Body Constituted by Dots

The nanometal body 21 may include a plurality of dots arranged as shown in FIGS. 12A to 12G.

As shown in FIGS. 12A to 12G, the shape of dots 22 viewed from above (in a plan view) is, for example, circular. When dots 22 are circular in shape in a plan view, the three-dimensional structure thereof is cylindrical, conical, spherical, etc. Alternatively, although not shown in the drawings, the shape in a plan view may be elliptical or polygonal. For example, when the dots 22 are polygonal in shape in a plan view, the three-dimensional structure thereof is a polygonal column, a polygonal cone, or a polyhedron.

The short part of each of the dots 22 (when the dots are circular, this is the diameter; when the dots are elliptical, this is the minor axis; and when the dots are polygonal, this is the short side of the smallest rectangle that can contain the polygon) is equal to or smaller than the wavelength. The distance between the dots 22 (the distance between the centers of the adjacent dots) is preferably equal to or lower than the wavelength.

Figure 12A:
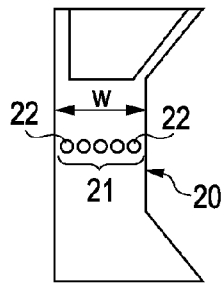
FIGS. 12A to 12G are plan views illustrating modification examples of nanometal bodies.

For example, as shown in FIG. 12A, the nanometal body 21 may include dots 22 lined up in a row at regular intervals. The direction in which the dots 22 are arranged is parallel to the direction of the width w of the ridge 20, for example.

Figure 12B:
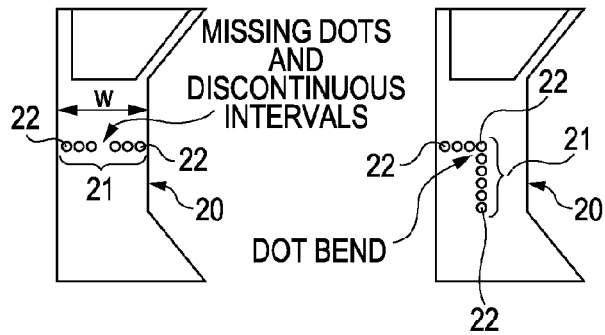

For example, as shown in FIG. 12B, the nanometal body 21 may include dots 22 lined up in a row at regular intervals but with a missing dot or a discontinuous point. The direction in which the dots 22 are arranged is parallel to the direction of the width w of the ridge 20, for example. When the dots 22 are arranged into a straight line, missing dots or discontinuous points are preferably provided over the entire row of the dots 22. In this manner, the Q value of the dot row positioned above the active layer 13 (not shown) is improved and the E-SP efficiency of spaser diodes is improved.

Figure 12C:
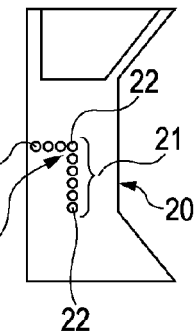

For example, as shown in FIG. 12C, the nanometal body 21 may include dots 22 lined up in a row at regular intervals but the line is bent from a particular point. According to this layout, the line is bent by 90°, but the angle of bending is not particularly limited. According to such a bent dot arrangement, reflection of the propagating surface plasmons occurs at the bent portion of the line. Thus, the Q value of the dot row positioned above the active layer 13 (not shown) is improved and the E-SP efficiency of spaser diodes is improved.

Figure 12D:
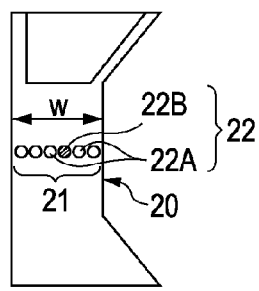

For example, as shown in FIG. 12D, the nanometal body 21 may include dots 22 (dots 22A and 22B) lined up in a row at regular intervals but a dot 22B composed of a material different from other dots, i.e., dots 22A, may be included in the line. The direction in which the dots 22 are arranged is parallel to the direction of the width w of the ridge 20, for example.

When the dots 22 are arranged in a straight line, the dots 22B composed of a different material are preferably provided over the entire row. Since reflection of the propagating surface plasmons occurs at the discontinuous point of the metal material of the dots 22, the Q value of the dot row positioned above the active layer 13 (not shown) is improved and the E-SP efficiency of spaser diodes is improved.

Figure 12E:
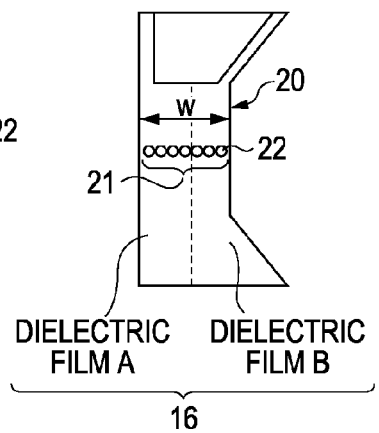

For example, as shown in FIG. 12E, the nanometal body 21 may include dots 22 lined up in a row at regular intervals. The direction in which the dots 22 are arranged is parallel to the direction of the width w of the ridge 20, for example.

The materials of the dielectric films formed on the lower surface, the upper surface, or both the lower and upper surfaces of the dot row may be discontinuous. For example, the insulating film 16 may be constituted by a dielectric film A and a dielectric film B which are composed of different materials.

Since reflection of the propagating surface plasmons occurs at the discontinuous point between different dielectric materials (e.g., insulating film 16), the Q value of the dot row positioned above the active layer 13 (not shown) is improved and the E-SP efficiency of spaser diodes is improved.

Figure 12F:
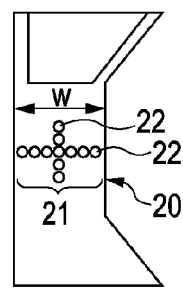

For example, as shown in FIG. 12F, the nanometal body 21 may include dots 22 arranged in two intersecting rows. For example, a first row of the dots 22 extends in parallel to the width w direction of the ridge 20 and a second row of the dots 22 extends in a direction perpendicular to the width w direction of the ridge 20. The first row and the second row intersect each other to form a cross shape. When the dot rows intersect each other and the near-field light from the cleaved surface of the ridge 20 is to be used, the resonance spectrum can be shaped.

Figure 12G:
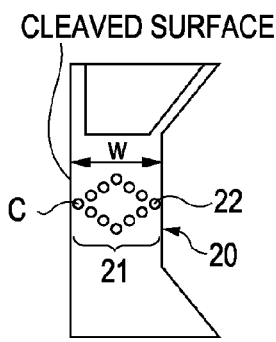

For example, as shown in FIG. 12G, the waveguide constituted by dots may be closed. According to the example shown in the drawing, the dots 22 are arranged into a parallelogram (e.g., rhombus). Such a closed arrangement may be, for example, annular. Since a closed dot arrangement forms a ring resonator, the Q value is increased. Moreover, when the closed resonator constituted by a closed dot row has an angular portion (where the row is bent) C, intense near-field light may be generated at the bent portion C. Thus, the bent portion C is preferably positioned near the cleaved surface of the ridge 20.

Examples of the Main Material of the Nanometal Body

The nanometal body 21 may be composed of a single metal such as gold (Au), silver (Ag), aluminum (Al), or the like or an alloy that contains as a main material at least one metal selected from gold (Au), silver (Ag), and aluminum (Al), as described above. The nanometal body 21 may contain at least one metal selected from platinum (Pt), nickel (Ni), and palladium (Pd).

Examples of Surface Protection Film of Nanometal Body

The nanometal bodies 21 described above are dependent on the wavelength of the light.

Nanometal bodies 21 containing of silver (Ag) or aluminum (Al) can be used in a wide wavelength range, i.e., from ultraviolet to infrared range and in a longer wavelength range. The nanometal bodies 21 containing Ag or Al are easily oxidizable. Thus, a surface protective film such as a dielectric film composed of silicon nitride (SiN), aluminum nitride (AlN), or the like is preferably formed on the surface of the nanometal body 21 to prevent oxidation. A refractory metal thin film may also be used as the surface protection film. A composite film of a refractory metal thin film and an inoxidizable metal thin film such as gold (Au) or platinum (Pt) may also be used.

The thickness of the surface protection film is preferably 5 nm or less. When the thickness of the surface protection film is larger than 5 nm, generation of surface plasmons may be inhibited. Moreover, the thickness of the surface protection film is desirably 1 nm or more to prevent passage of oxygen.

Examples of Main Material of Nanometal Body

Trace amounts of other elements may also be added to the main material such as silver (Ag) and aluminum (Al). "Main material" means that a total of 90% or more of Ag and Al is contained in the nanometal body.

When the nanometal bodies 21 are composed of gold (Au), the nanometal bodies 21 can be used in the wavelength of about 500 nm to the infrared range and a longer wavelength range. Since gold (Au) is inoxidizable, covering the surface with the surface protection film is not needed. However, the resonant frequency can be adjusted and the durability can be improved by coating the surface of the nanometal body 21 with an appropriate dielectric film composed of, for example, silicon oxide ($SiO_2$), silicon nitride (SiN), aluminum oxide ($Al_2O_3$), or the like. Trace amounts of other elements may be added to the gold main material (Au). Here, "main material"

means that gold is contained in an amount of 90% or more. When the main material is contained in an amount of 90% or more, the characteristics of the main material can be fully displayed.

Alternatively, at least two elements selected from Au, Ag, and Al may be used as the main materials and trace amounts of other elements may be added to the main materials. For example, in the near infrared range to the infrared range and in a longer wavelength range, at least one element selected from platinum (Pt), nickel (Ni), and palladium (Pd) may be contained as a main material. Trace amounts of other elements may be added.

At least one element selected from Au, Ag, Al, Pt, Ni, and Pd may be contained as a main material. Trace amounts of other elements may be added.

The active layer 13 of the surface plasmon-generating apparatus 1 having the above-described structure has a transverse junction structure (TJS). When viewed in the perpendicular direction, the TJS is included in a semiconductor multilayer structure including, in order from the bottom, the first barrier layer 12, the active layer 13, and the second barrier layer 14. Moreover, the TJS is limited in the horizontal direction by the pn homojunction and in the length direction by a restricting structure of the ridge 20 having a narrow width.

Thus, according to the surface plasmon-generating apparatus 1, when an electric current is injected into the homojunction, electron-hole pairs are generated in the limited region of the ridge 20. In other words, the injected electrons and holes efficiently form electron-hole pairs in the homojunction under the nanometal body 21 and a nearby region. The nanometal body 21 formed near the active layer 13 in the perpendicular direction receives energy from the electron-hole pairs and generates surface plasmons.

When the nanometal body 21 has a structure that can structurally resonate at a wavelength corresponding to the emission spectrum of the homojunction, coherent surface plasmons can be generated. Thus, a spaser diode of a current injection type can be provided.

Moreover, according to the surface plasmon-generating apparatus 1 described above, when a voltage V1 is applied between the p electrode 18 and the n electrode 19, relationship (1), i.e., Eg1<V1 is satisfied where Eg1 represents the bandgap energy of the active layer 13.

Preferably, V1<Eg2 or Eg3 (relationship (2)) where Eg2 represents the bandgap energy of the first barrier layer 12 and Eg3 represents the bandgap energy of the second barrier layer 14 since the electric current is narrowed toward the homojunction of the ridge 20.

In other words, the bandgaps of the first barrier layer 12 and the second barrier layer 14 are preferably sufficiently large.

The distance between the active layer 13 and the nanometal body 21 is preferably as small as possible. Accordingly, the thickness of the second barrier layer 14 is 1 nm to 50 nm and preferably 4 nm or more and 10 nm or less. When the thickness of the second barrier layer 14 is less than 1 nm, quantum confinement of holes is not achieved. The thickness is preferably about the Bohr radius, i.e., 4 nm or more. When the thickness exceeds 10 nm, the efficiency of generating surface plasmons may decrease. Accordingly, the thickness of the second barrier layer 14 is 1 nm to 50 nm and preferably 4 nm or more and 10 nm or less.

The insulating film 16 is provided to electrically isolate the semiconductor multilayer structure from the nanometal body 21 and the thickness of the insulating film 16 is preferably 3 nm or more and 10 nm or less.

Thus, the distance between the active layer 13 and the nanometal body 21 is 20 nm or less and the electromagnetic field generated by the surface plasmons of the nanometal body 21 overlaps the homojunction in the active layer 13. The thickness of the n-type first barrier layer 12n and the p-type first barrier layer 12p is each 1 nm to 50 nm and preferably 10 nm or less. When the thickness is less than 1 nm, the crystallinity is degraded, the non-radiative recombination probability is increased, and thus the E-SP efficiency is decreased. In contrast, when the thickness is larger than 50 nm, the injection current increases; in other words, the power consumption increases.

In particular, when the thickness of the second barrier layer 14 is 10 nm or less, tunneling of holes between the intermediate layer (e.g., AlGaAs layer) and the active layer 13 (e.g., GaInP layer) occurs through the second barrier layer 14 (e.g., AlGaInP layer). This decreases the driving voltage.

2. Second Embodiment

Example of Method for Making Surface Plasmon-Generating Apparatus

An example of a method for making a surface plasmon-generating apparatus according to a second embodiment will now be described with reference to FIG. 1.

The surface plasmon-generating apparatus 1, which is a spaser diode described above, can be made as follows.
Formation of Semiconductor Multilayer Structure Referring to FIG. 1, a semiconductor multilayer structure is formed on a substrate 11 by, for example, metal organic chemical vapor deposition (MOCVD). A gallium arsenide (GaAs) substrate is used as the substrate 11, for example.

The semiconductor multilayer structure is formed by, for example, sequentially layering a buffer layer (not shown), a first barrier layer 12 of a first conductivity type (e.g., n-type), an n-type active layer 13, an n-type second barrier layer 14, an intermediate layer (not shown), and a cap layer-forming layer for forming a cap layer 15 of a second conductivity-type (p-type) on the substrate 11.

The buffer layer is formed by depositing gallium indium phosphide (GaInP). The first barrier layer 12 is formed by depositing n-type aluminum gallium indium phosphide (n-AlGaInP). The active layer 13 is formed by depositing n-type gallium indium phosphide (n-GaInP). The second barrier layer 14 is formed by depositing n-type aluminum gallium indium phosphide (n-AlGaInP).

The intermediate layer is formed by depositing aluminum gallium arsenide (AlGaAs). The cap-forming layer for forming the p-type cap layer 15 is formed by depositing gallium arsenide (p-GaAs), for example.

The raw materials used for epitaxially growing the individual layers are selected from, for example, trimethyl aluminum (TMAl), trimethyl gallium (TMGa), trimethyl indium (TMIn), phosphine ($PH_3$), and arsine ($AsH_3$). Monosilane ($SiH_4$) is used as the raw material for the donor impurity, for example. Biscyclopentadienyl magnesium ($Cp_2Mg$), dimethyl zinc (DMZn), or the like is used as the raw material for the acceptor impurity, for example.
Formation of Impurity Diffusion Source Then a zinc oxide (ZnO) film is formed on the cap layer-forming layer above a region that will form a p-type region in the semiconductor multilayer structure. The zinc oxide film is formed on the cap layer-forming layer to a thickness of, for example, about 50 nm to about 500 nm. A hard mask technique, a lift-off technique, an etching technique, and the like can be used as the technique for patterning the zinc oxide film.

For example, when a hard mask technique is employed, the zinc alloy film is formed by the following process. A silicon nitride (SiN) film having a thickness of about 50 nm to about 300 nm is formed as a hard mask layer on the cap layer-forming layer. Then the hard mask layer is patterned by a common etching technique using a resist mask to form an opening (not shown) on the region will form the p-type region. After the resist mask is removed, a zinc oxide film is formed on the hard mask layer. The zinc oxide film contacts the cap layer-forming layer in the opening of the hard mask layer.

As a result, the portion where the zinc oxide film contacts the cap layer-forming layer can be made to correspond to the impurity-diffused region. Alternatively, the hard mask layer may be a silicon oxide ($SiO_2$) film.

For example, when a lift-off technique is employed, the zinc alloy film is formed by the following process. A resist is applied on the cap layer-forming layer to form a resist thick film. Then part of the resist thick film above the region corresponding to the impurity-diffused region is removed to form an opening. Then a zinc oxide film is formed on the resist film to allow the zinc oxide film to contact the cap layer-forming layer in the opening formed in the resist film. The zinc oxide film is preferably deposited anisotropically and is preferably thinner than the resist film. Then the resist film is removed to remove the zinc oxide film formed on the resist film and to allow the zinc oxide film to remain inside the opening formed in the resist film.

As a result, the portion where the zinc oxide film contacts the cap layer-forming layer can be made to correspond to the impurity-diffused region.

For example, when an etching technique is employed, the zinc alloy film is formed by the following process. A zinc oxide film is formed over the entire surface of the cap layer-forming layer. A resist is applied to form a resist film and the resist film is lithographically patterned to form a resist mask on a region corresponding to the impurity-diffused region. Next, the zinc oxide film is etched using the resist mask as an etching mask. For example, a hydrochloric acid-based etchant is used in this etching. As a result of the etching, the zinc oxide film remains only on the region corresponding to the impurity-diffused region.

After the zinc oxide film that serves as a diffusion source of the p-type impurity is formed as such, the zinc oxide film is covered with a silicon oxide ($SiO_2$) film, for example. When the zinc oxide film is covered with the silicon oxide film, the zinc atoms are prevented from escaping into the vapor phase in the subsequent annealing step.

Formation of P-Type Region by Diffusing Impurity

Next, annealing is conducted for about several to thirty minutes at a temperature of 500° C. to 600° C. in, for example, an inert atmosphere such as a nitrogen ($N_2$) atmosphere. As a result, the zinc (Zn) atoms contained in the zinc oxide film diffuse into the second barrier layer 14, the active layer 13, and the first barrier layer 12 through the cap layer-forming layer. The diffused zinc (Zn) atoms act as acceptors.

The diffused region is a co-doped region in which silicon and zinc are diffused and can function as a p-type semiconductor due to diffusion of a sufficient number of zinc atoms.

Preferably, the active layer (p-type active layer 13) in the zinc-diffused region contains zinc atoms in a concentration of $1 \times 10^{17}$ atoms/cm$^3$ to $5 \times 10^{18}$ atoms/cm$^3$.

Next, if desired, annealing is conducted for about 10 to 120 minutes at a temperature of about 650° C. to about 750° C. in a nitrogen ($N_2$) atmosphere or an arsine ($AsH_3$) atmosphere, for example. As a result of this annealing, the zinc (Zn) atoms diffused into the semiconductor multilayer structure unfailingly occupy the group 13 (group III) sites and the crystallinity of the semiconductor multilayer structure is improved.

Whether the crystallinity of the semiconductor multilayer structure has improved or not can be confirmed through measuring the photoluminescence (PL) and observing whether the emission from a deep level spreading broadly in the long wavelength range is suppressed or not.

The p-type second barrier layer 14p is formed in the n-type second barrier layer 14n, the p-type active layer 13p is formed in the n-type active layer 13n, and the p-type first barrier layer 12p is formed in the n-type first barrier layer 12n by the diffusion process described above.

The zinc concentration rapidly drops at the zinc-diffused region boundary in the semiconductor multilayer structure, and the conductivity type changes from the p-type to the n-type through the i-type. Accordingly, a TJS structure is formed in which a pn junction is formed in the plane in the perpendicular direction of the semiconductor multilayer structure.

Next, the silicon oxide ($SiO_2$) film is removed by, for example, wet etching using a buffered hydrofluoric acid and the zinc oxide film is removed by wet etching using a hydrochloric acid-based etchant. When the hard mask technique is used and the hard mask layer is formed as a silicon nitride film, the hard mask layer is removed by wet etching using hot phosphoric acid. When the hard mask layer is formed as a silicon oxide film, the hard mask layer is removed simultaneously with the silicon oxide layer described above.

Formation of Ridge

Next, after a resist film is formed on the entire surface of the cap layer-forming layer by a resist application technique, the resist film is exposed and developed using a common lithography technique to leave the resist film inside the impurity-diffused region. This resist film serves as an etching mask for forming the p-type cap layer. The cap layer-forming layer and the intermediate layer are etched using the resist film as an etching mask. As a result, the p-type cap layer 15 is formed from the cap layer-forming layer and the intermediate layer is formed underneath.

The etching is conducted by using a phosphoric acid-based etchant, for example, to etch the cap layer-forming layer and the AlGaAs intermediate layer. Since the base of the intermediate layer is an AlGaInP layer, the etching rate against the phosphoric acid-based etchant is sufficiently low. Thus, the outermost surface of the etched portion forms the second barrier layer 14 which is an AlGaInP layer. Then the resist mask is removed.

Next, a resist film is formed on the entire surface of the second barrier layer 14 by a resist application technique to cover the p-type cap layer 15. Then the resist film is exposed and developed by a common lithography technique to leave the resist mask on the region where the ridge is to be formed. At this stage, the p-type cap layer 15 is covered with the resist mask.

Next, the second barrier layer 14, the active layer 13, and the first barrier layer 12 are sequentially etched in that order by using the resist mask as the etching mask to form the ridge 20 including the second barrier layer 14, the active layer 13, and the upper part of the first barrier layer 12. For example, a hydrochloric acid-based etchant is used in this etching.

Then the resist mask used in the etching is removed.

Formation of Insulating Film

Next, an insulating film 16 is formed as a dielectric film composed of silicon oxide ($SiO_2$) or the like covering the entire surfaces of the p-type cap layer 15 and the ridge 20, etc.

The thickness of the insulating film 16 is preferably 3 nm or more and 10 nm or less, for example. A common insulating film may be used as the insulating film 16.

Formation of Nanometal Body

A nanometal body 21 is then formed on the insulating film 16 of the ridge 20 to extend across the pn junction formed in the active layer 13.

When the nanometal body 21 is isolated from the surrounding structures, the nanometal body 21 may be made by using a thin film resist for electron beam lithography and conducting a lift-off process.

Common nano processes such as nano imprinting may also be used.

Alternatively, a metal film may be formed on a patterned UV-curable resin or thermosetting resin and patterned by a lift-off process to form the nanometal body 21.

Alternatively, a nano pattern several to several hundred nanometers in size, for example, 3 nm to 300 nm in size, may be formed by etching.

For example, after a metal thin film is formed on the insulating film 16, the metal thin film is processed with a focused ion beam (FIB) to form the nanometal body 21. Alternatively, the nanometal body 21 is formed by forming a resist film on a metal thin film by application, patterning the resist film to form a resist mask, and wet- or dry-etching the metal thin film using the resist mask as the etching mask.

As a result, a nanometal body 21 several to several hundred nanometers in size is formed.

The metal thin film may be a plate-like thin film or a film constituted by nano dots. An appropriate selection may be made.

Formation of p Electrode

A dielectric film (not shown) is formed on the entire surfaces of the nanometal body 21, the ridge 20, etc. The dielectric film is preferably formed to have a thickness of about 50 nm or more and about 250 nm or less.

Next, the dielectric film on the p-type cap layer 15 is removed by common etching using a resist mask to form an opening. Then the resist mask is removed.

An electrode-forming film is formed on the dielectric film to allow the electrode-forming film to contact the p-type cap layer 15 in the opening formed in the dielectric film. The electrode-forming film here is preferably deposited anisotropically and is preferably thinner than the dielectric film.

The electrode-forming film is formed by sequentially depositing a titanium (Ti) film, a platinum (Pt) film, and a gold (Au) film in that order from the bottom. The electrode-forming film is not limited to the above-described multilayer structure and may have any other multilayer structure.

Subsequently, the dielectric film is removed by a lift-off technique to also remove the electrode-forming film on the dielectric film. The electrode-forming film remains in the opening formed in the electrode-forming film and forms the p electrode 18.

Formation of n Electrode

Next, an n electrode 19 is formed on the back side of the substrate 11 which is an n-GaAs substrate. The n electrode 19 is constituted by, from the substrate 11 side, gold germanium (AuGe) layer/nickel (Ni) layer/gold (Au) layer/titanium (Ti) layer/platinum (Pt) layer/gold (Au) layer, for example. Then alloying is conducted at an atmosphere temperature of 250° C. or more.

The multilayer structure of the n electrode 19 is not limited to the above-described structure and may be a multilayer structure including other metal films. Moreover, the n electrode 19 may be a single layer.

Formation of Chip

The substrate 11 is cleaved so that the nanometal body 21 is cut in parallel to the y-z plane, for example. The cleaved surface formed by the cleavage may be formed by dry- or wet-etching. Other surfaces are also cut by cleaving or dicing to form a surface plasmon-generating apparatus 1 including a spaser diode.

Alternatively, a wafer may be cut to form an array of spaser diodes connected to each other.

The surface plasmon-generating apparatus 1 may be formed by film-forming methods other than the MOCVD method. For example, films may be formed by molecular beam epitaxy (MBE), liquid phase epitaxy (LPE), electron beam deposition, sputtering, plasma-enhanced CVD, and laser ablation depending on the semiconductor materials.

As for the dopant of the semiconductor layers, silicon (Si) and selenium (Se) may be used as the n-type dopant and zinc may be mainly used as the p-type impurity diffusion source. As mentioned above, p-type regions may be formed by a solid diffusion technique described above, a gas phase diffusion technique, an ion injection technique, or the like. The technique for forming films is not particularly limited in the manufacturing method described above.

Since the nanometal body 21 formed by the manufacturing method described above has a fine structure, process errors occur during the manufacturing process and the edges of the nanometal body 21 may not be strictly defined and may sometimes be rounded. However, this poses no problem.

The active layer 13 of the surface plasmon-generating apparatus 1 having the above-described structure has a transverse junction structure (TJS). When viewed in the perpendicular direction, the TJS is included in a semiconductor multilayer structure including, in order from the bottom, the first barrier layer 12, the active layer 13, and the second barrier layer 14. Moreover, the TJS is limited in the horizontal direction by the pn homojunction and in the length direction by a restricting structure of the ridge 20 having a narrow width.

Thus, according to the surface plasmon-generating apparatus 1, when an electric current is injected into the homojunction, electron-hole pairs are generated in the limited region of the ridge 20. In other words, the injected electrons and holes efficiently form electron-hole pairs in the homojunction under the nanometal body 21 and its nearby region. The nanometal body 21 formed near the active layer 13 in the perpendicular direction receives energy from the electron-hole pairs and generates surface plasmons.

When the nanometal body 21 has a structure that can structurally resonate at the wavelength corresponding to the emission spectrum of the homojunction, coherent surface plasmons can be generated. Thus, a spaser diode of a current injection type can be realized.

According to the method for making the surface plasmon-generating apparatus described above, the nanometal body 21 is formed on the insulating film 16 above the pn junction of the active layer 13 to extend across the pn junction formed in the active layer 13. Thus, when an electric current is injected into the pn junction of the active layer 13, the injected electrons and holes efficiently form electron-hole pairs in the pn junction under the nanometal body 21 and its nearby region. The nanometal body 21 formed near the active layer 13 in the perpendicular direction receives energy from the electron-hole pairs and generates surface plasmons. The surface plasmon-generating apparatus 1 formed by the method described above displays a high E-SP efficiency since surface plasmons can be directly generated by current injection.

Examples of Application of Surface Plasmon-Generating Apparatus

The front surfaces of the substrate 11 and the semiconductor multilayer structure shown in FIG. 1 are usually formed by cleavage. Thus, surface plasmons generated on the nanometal body are accessible from the front surfaces as shown in FIG. 3.

This spaser diode can be used in the following applications.

An example of an information recording apparatus to which the surface plasmon-generating apparatus 1 is applied will now be described with reference to FIGS. 13 and 14A to 14C.

Figure 13:
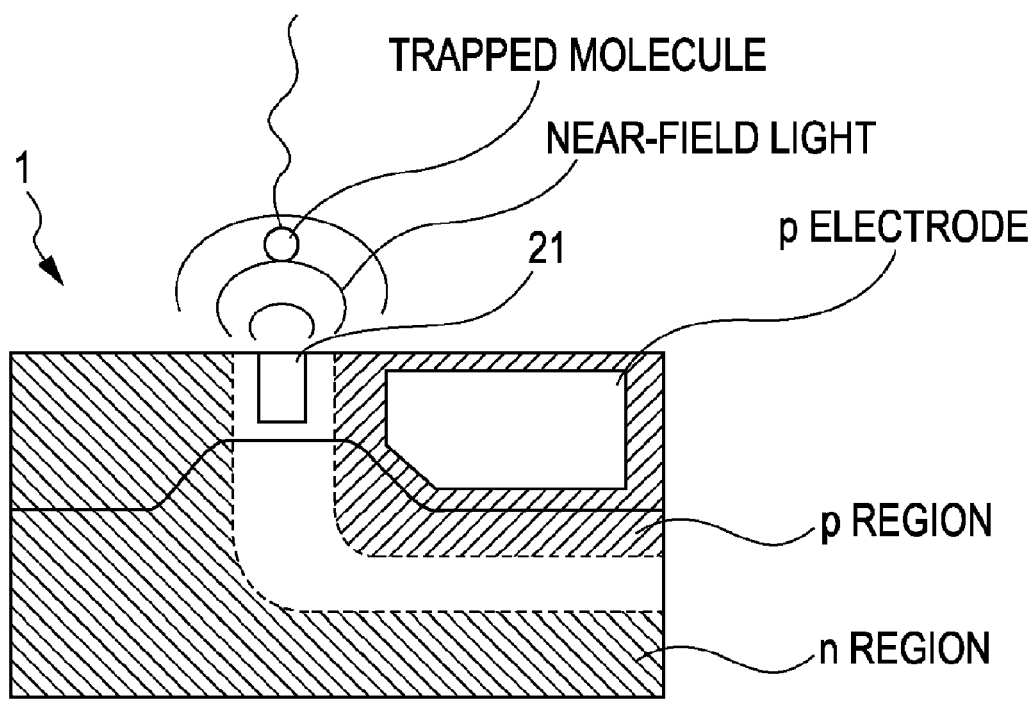
FIG. 13 is a plan view showing an application example of a surface plasmon-generating apparatus.

The surface plasmon-generating apparatus 1 shown in FIG. 13 has the structure described with reference to FIG. 1 etc. Molecules and fine particles can be captured by high-intensity near-field light generated at the front surface by surface plasmons generated by the nanometal body 21. The surface plasmon-generating apparatus 1 can be used in biosensing, optical molding, and acceleration of selective chemical reactions.

Figure 14A:
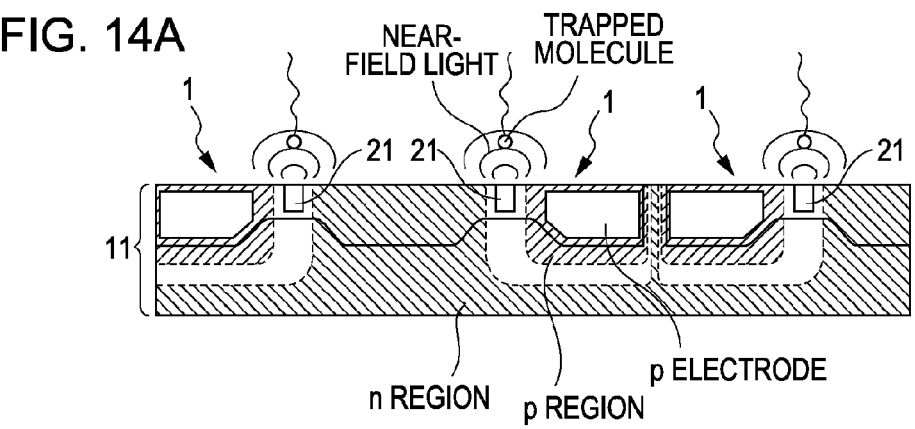
FIGS. 14A and 14B are plan views and FIG. 14C is a perspective view illustrating application examples of a surface plasmon-generating apparatus.

Referring to FIG. 14A, the surface plasmon-generating apparatuses 1 serving as spaser diodes described with reference to FIG. 1 are arranged in one row on the substrate 11. In this structure, the intervals of the nanometal bodies 21 are several ten micrometers or more. Highly intense near-field light is generated at the front surface by surface plasmons generated by the surface plasmon-generating apparatuses 1. Molecules and fine particles can be captured by this near-field light. According to this array structure, molecules and fine particles can be captured at a desired cycle and position.

Figure 14B:
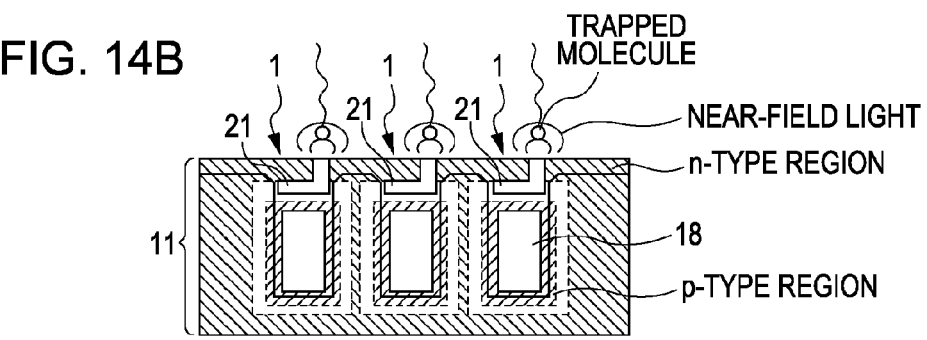

Referring now to FIG. 14B, the surface plasmon-generating apparatuses 1 serving as spaser diodes are arranged in a row on the substrate 11. Due to the spaser diode array structure, molecules and fine particles can be captured at a desired cycle and position. According to this structure, the nanometal body 21 is formed to have an L shape in a plan view, for example. The nanometal body 21 and a p-type region including a p-type first barrier layer, a p-type active layer, and a p-type second barrier layer (not shown) are arranged in a direction perpendicular to the direction in which the surface plasmon-generating apparatuses 1 forming the array are aligned in a plan view. A p-type cap layer (not shown) and a p electrode are formed on the p-type region (p-type second barrier layer not shown in the drawing). Thus, the nanometal bodies 21 and the p-type regions are arranged to be adjacent to each other through an n-type region including an n-type first barrier layer, an n-type active layer, and an n-type second barrier layer (not shown).

When the nanometal bodies 21 and the p electrodes 18 are arranged as such, the nanometal bodies 21 can be arranged close to each other.

The structure of the nanometal body 21 having an L shape in a plan view is merely an example and various structures described above can be employed. A small portion of the nanometal body 21 lies above the n-type region and the majority of the nanometal body 21 lies above the pn junction. Since the n-type region, the pn junction, and the p-type region are arranged in that order from the cleaved surface, the intervals between the nanometal bodies 21 can be reduced to 10 µm or less in size.

Figure 14C:
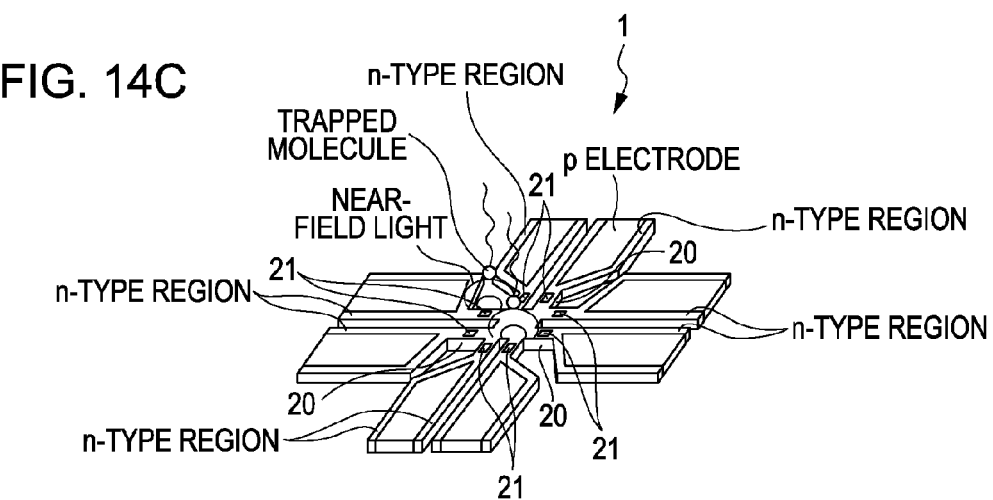

FIG. 14C is a perspective view of a structure in which a plurality (eight in the drawing) of ridges 20 having a common n-type region are connected at a central portion. Nanometal bodies 21 are arranged in the central portion of the corresponding ridges 20. The nanometal bodies 21 can be locally arranged in a two dimension as such. According to this structure, since the near-field light is accessed from above the surface, the trapped molecules extend above the wafer surface. This structure can also be applied to a single-element spaser diode.

Moreover, according to this structure, since the orientation of the molecules and the fine particles can be designated at particular positions, a molecular-size three-dimensional artificial structure can be formed. This is what is generally called a bottom-up nanofabrication. Moreover, different molecules and fine particles can be captured by changing the resonant frequency of the nanometal bodies 21 of the respective surface plasmon-generating apparatuses 1 (spaser diodes).

The apparatus can be used as a light source for an information recording apparatus that uses highly intense near-field light.

Figure 15A:
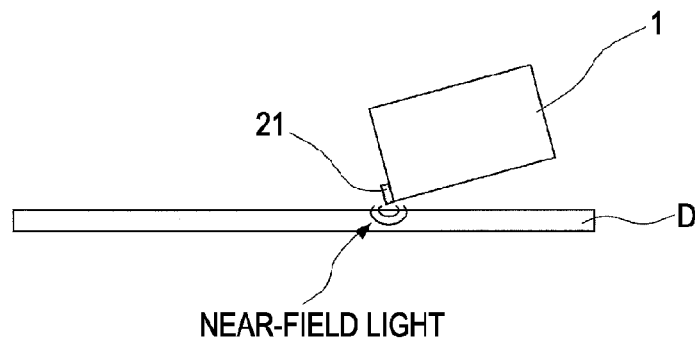
FIGS. 15A and 15B are respectively a front view and a perspective view illustrating application examples of a surface plasmon-generating apparatus.

For example, as shown in FIG. 15A, in order to use mainly or secondarily, the nanometal body 21 of the surface plasmon-generating apparatus 1 (spaser diode) is preferably brought close to the information recording medium D. However, since the nanometal body 21 is located on the cleaved interface, the nanometal body 21 can be easily brought close to the information recording medium D.

Figure 15B:
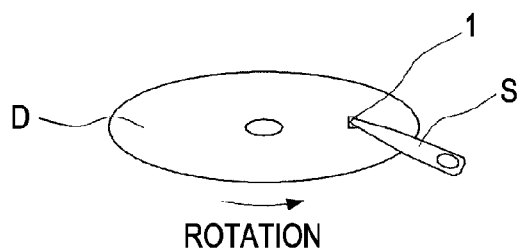

An air bearing surface (ABS) structure may be formed on the cleaved surface. For example, as shown in FIG. 15B, the information recording medium D may be a disk and the surface plasmon-generating apparatus 1 (spaser diode) may be attached onto a suspension S commonly used in hard disk drives (HDDs) so that the position of the surface plasmon-generating apparatus 1 can be controlled as desired.

As shown in FIGS. 14A to 14C, when the surface plasmon-generating apparatuses 1 (spaser diodes) are arranged into an array structure, simultaneous recording and playing is made possible and thus the recording density is improved. The apparatus can be used as a light source for a near-field light exposure apparatus that uses highly intense near-field light. In particular, when the surface plasmon-generating apparatuses 1 (spaser diodes) are arranged into an array structure, the throughput can be improved.

Although not shown in the drawing, the surface plasmon-generating apparatus 1 (spaser diode) may be directly built into a plasmonic circuit. In such usages, cleavage is not necessary and many surface plasmon-generating apparatuses 1 are formed in a wafer surface.

Normally, the n electrode 19 is common to the surface plasmon-generating apparatuses 1 and each surface plasmon-generating apparatus 1 is driven by an independent p-electrode 18. The nanometal bodies 21 of respective surface plasmon-generating apparatuses 1 are coupled through plasmonic waveguides and together function as a circuit. In this manner, the circuit can be driven at a high efficiency. Moreover, since the surface plasmon-generating apparatuses 1 can be arranged close to each other and driven independently, the size of the circuit can be reduced.

Figure 16:
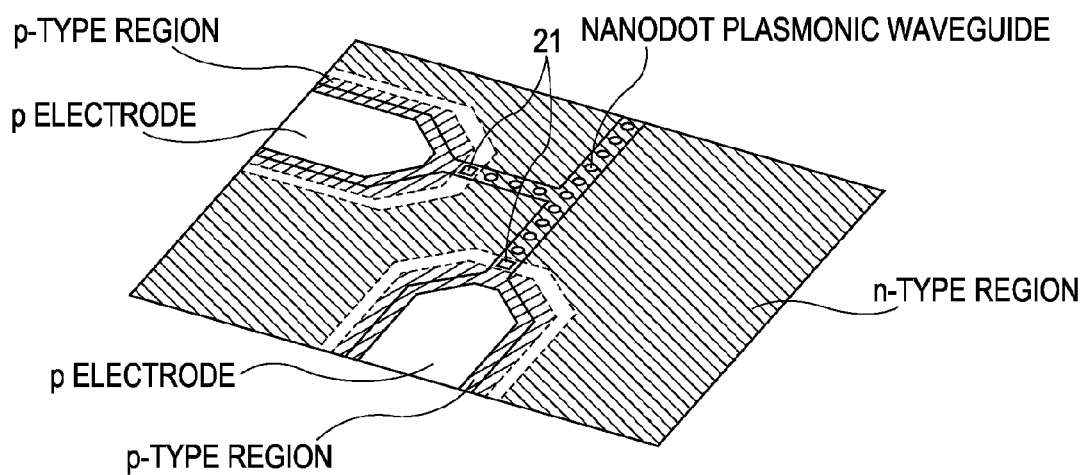
FIG. 16 is a perspective plan view illustrating an application example of a surface plasmon-generating apparatus.

When a plasmonic waveguide is formed above the second barrier layer 14 (not shown) composed of n-AlGaInP as shown in FIG. 16, the plasmonic waveguide can be arranged at the same height as the nanometal body 21 of the surface plasmon-generating apparatus. In the drawing, an example in which nanodot rows are used to form the plasmonic waveguide and two paths are coupled is illustrated.

Even when the intervals between the nanometal bodies 21 are small as shown in FIG. 14C, ends of different plasmonic waveguides may be arranged close to one another via the plasmonic waveguide described above.

The present application contains subject matter related to that disclosed in Japanese Priority Patent Application JP 2009-141774 filed in the Japan Patent Office on Jun. 15, 2009, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A surface plasmon-generating apparatus comprising:
an active layer including an n-type region formed on one side and a p-type region formed on the other side, the n-type region and the p-type region being in contact with each other to form a pn junction therebetween;
a first barrier layer in contact with a first surface of the active layer;
a second barrier layer in contact with a second surface of the active layer, the second surface being opposite the first surface; and
a metal body disposed above the pn junction of the active layer with the second barrier layer and an insulating layer therebetween,
wherein,
a part of the first barrier layer and a part of the second barrier layer that sandwich the p-type region of the active layer are formed to be p-type, and
a part of the first barrier layer and a part of the second barrier layer that sandwich the n-type region of the active layer are formed to be n-type.

2. The surface plasmon-generating apparatus according to claim 1, wherein the first barrier layer is composed of a semiconductor having a bandgap energy larger than a bandgap energy of the active layer.

3. The surface plasmon-generating apparatus according to claim 1, wherein the second barrier layer is composed of a semiconductor having a bandgap energy larger than a bandgap energy of the active layer.

4. The surface plasmon-generating apparatus according to claim 1, wherein a multilayer structure including the first barrier layer, the active layer, and the second barrier layer is formed as a ridge having a ridge shape, and the pn junction of the active layer is formed within the ridge.

* * * * *